United States Patent
Keller

(10) Patent No.: US 7,217,057 B2
(45) Date of Patent: May 15, 2007

(54) SURGICAL IMPLANT OR INSTRUMENT WITH FIXING SCREW

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 89 days.

(21) Appl. No.: 11/058,694

(22) Filed: Feb. 16, 2005

(65) Prior Publication Data

US 2005/0141985 A1    Jun. 30, 2005

Related U.S. Application Data

(63) Continuation of application No. PCT/EP03/07942, filed on Jul. 21, 2003.

(30) Foreign Application Priority Data

Aug. 16, 2002   (DE)   ............... 202 12 600

(51) Int. Cl.
*F16B 1/12*    (2006.01)

(52) U.S. Cl. ............... 403/109.3; 403/109.1; 403/109.4; 403/109.6; 403/362; 403/379.3; 411/393; 606/62; 606/64

(58) Field of Classification Search ............ 403/109.1, 403/109.3, 109.4, 109.5, 109.6, 362, 379.3, 403/379.4, 379.5; 411/393; 606/62–64
See application file for complete search history.

(56) References Cited

U.S. PATENT DOCUMENTS

| | | | | |
|---|---|---|---|---|
| 3,074,589 A | * | 1/1963 | Chaney | 220/327 |
| 3,096,678 A | * | 7/1963 | Devine et al. | 411/64 |
| 3,270,610 A | * | 9/1966 | Knowlton | 411/427 |
| 5,387,048 A | * | 2/1995 | Kuo | 403/109.3 |
| 5,413,608 A | | 5/1995 | Keller | |
| 5,456,719 A | * | 10/1995 | Keller | 623/11.11 |
| 5,593,196 A | * | 1/1997 | Baum et al. | 294/19.1 |
| 6,006,477 A | * | 12/1999 | Ko | 135/25.4 |
| 6,099,569 A | | 8/2000 | Keller | |
| 6,409,203 B1 | * | 6/2002 | Williams | 280/506 |
| 6,409,768 B1 | * | 6/2002 | Tepic et al. | 623/23.27 |
| 6,626,604 B1 | * | 9/2003 | Pinarello | 403/196 |

FOREIGN PATENT DOCUMENTS

| | | |
|---|---|---|
| DE | 195 01 882 | 1/1995 |
| EP | 0 589 325 A1 | 9/1993 |
| EP | 1 031 322 A1 | 2/1999 |

* cited by examiner

*Primary Examiner*—Daniel P. Stodola
*Assistant Examiner*—Nahid Amiri
(74) *Attorney, Agent, or Firm*—Morrison & Foerster LLP

(57) ABSTRACT

A surgical implant or instrument has two parts, one sliding on the other, the lower part being provided with a threaded bore and the upper part being provided with a passage orifice for receiving a fixing screw. The set screw can be received over its entire length beneath the upper part in the threaded bore and includes, at its upper end, a dog point which is thinner than its threaded part and which is provided with a slit, groove or hexagon socket for a screwdriver, the diameter of the passage orifice being smaller than that of the threaded part and larger than that of the dog point. An elastic device is provided for the implant or instrument which pushes the fixing screw into the fixing position.

9 Claims, 1 Drawing Sheet

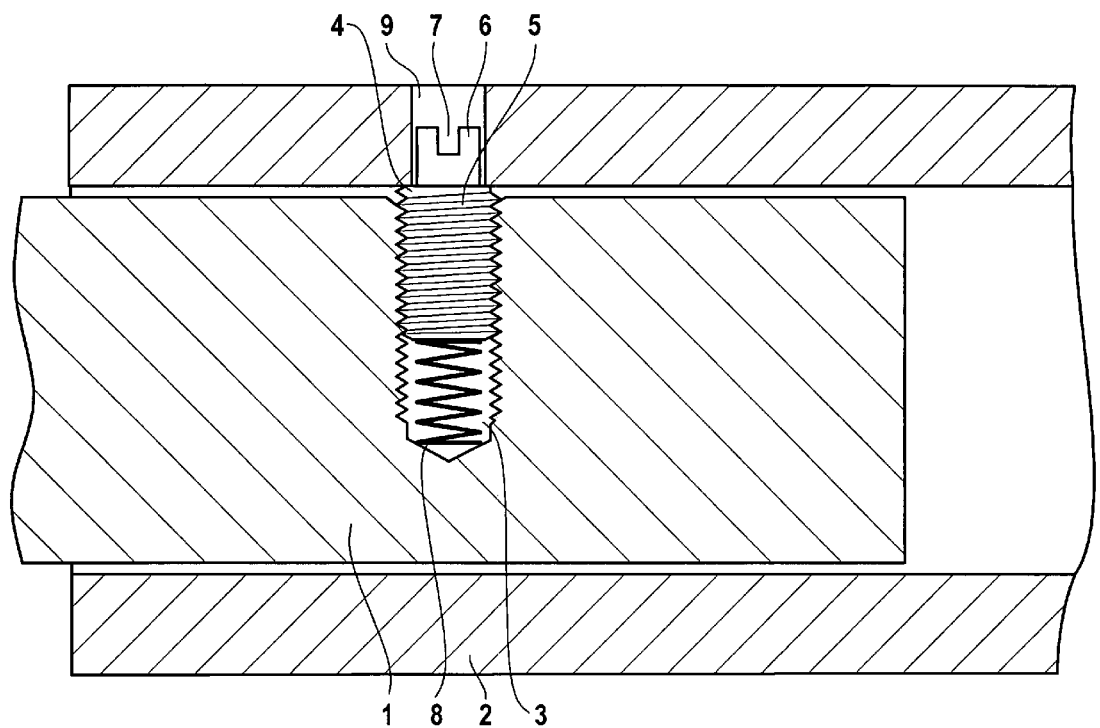

SURGICAL IMPLANT OR INSTRUMENT WITH FIXING SCREW

REFERENCE TO RELATED APPLICATIONS

This application is a continuation of International Application No. PCT/EP2003/007942, filed Jul. 21, 2003, which claims priority from German Application No. 202 12 600, filed Aug. 16, 2002, the disclosures of which are incorporated fully herein by reference.

FIELD OF THE INVENTION

The invention relates to a surgical implant or instrument with a fixing screw.

BACKGROUND OF THE INVENTION

In surgical implants or instruments, it is sometimes necessary to secure two mutually displaceably guided parts against displacement with a screw. It is known to do this by screwing a fixing screw through a passage orifice in the upper of the two parts and into a threaded bore in the lower of the two parts until its head sits firmly on the top face of the upper of the two parts. This has the disadvantage that the screw can be lost, which can have serious consequences in a confined operating site.

It is known (EP-A-589325, EP-A-1031332) to avoid this problem by using a screw which is designed as a set screw and can be accommodated over its entire length in the threaded bore and in any case beneath the lower face of the upper of the two parts. Such a screw has an upper, thinner dog point which contains a groove for a screwdriver. The diameter of the passage orifice is smaller than that of the screw thread but larger than that of the screw dog point. Before the parts are joined together, the screw is screwed into the threaded bore to such a depth that it disappears completely in the threaded bore or at any rate lies deep enough within the bore that the upper of the two parts can slide over it. The screwdriver is then engaged through the passage orifice of the upper part and is used to turn the screw upward until its dog point lies in the passage orifice. The two parts are now secured against relative displacement so long as the screw is turned tight. If the screw loosens, however, it may gradually drift downward to such an extent that the fixing action is compromised.

SUMMARY OF THE INVENTION

Therefore, one feature of the invention is to ensure more substantial fixing against the fixing screw falling back into the threaded bore. According to the invention, this is achieved by the fact that it is acted upon from the lower end by an elastic force, for example a spring. A surgical implant or instrument according to this invention includes an upper and a lower part, each of which is adapted for sliding on the other. The lower part has a threaded bore formed through it, and the upper part as a passage orifice formed in it for receiving a threaded fixing screw. The structure of the invention further includes an elastic device that is configured for pushing the fixing screw into a fixing position. The fixing screw is configured as a set screw and has a length such that the threaded bore can receive the fixing screw over its entire length beneath the upper part in the threaded bore. The fixing screw also has a dog point at its upper end which is thinner than the threaded portion of the fixing screw and is configured for receiving a screwdriver in a groove, slit or hexagon socket or other such conventional interface with a screwdriver. In addition, the diameter of the passage orifice has an inner diameter that is smaller than an inner diameter of the threaded bore and is larger than the diameter of the dog point.

The terms "upward" and "downward" as used in this application are not to be interpreted in the sense of an absolute or geodetic height, but instead signify the positions relative to the observer seeking access to the fixing screw. The lower part is, generally speaking, the part covered by the upper part.

BRIEF DESCRIPTION OF THE DRAWING

The invention is explained in greater detail below with reference to the single drawing which depicts an illustrative and non-limiting embodiment of the invention in cross section.

DETAILED DESCRIPTION OF THE INVENTION

A bolt 1 is to be connected to a sleeve 2 which, having a slightly greater diameter, is pushed over the bolt. Their interacting surfaces provide a guide which permits relative movement between the two parts only parallel to their longitudinal axis.

The bolt 1 has a threaded bore 3 extending transversely with respect to its longitudinal axis. The threaded screw 4, which has a threaded portion 5 and an upper dog point 6, sits in the threaded bore 3, and the upper dog point 6 has a slit or hexagon socket 7 for connection to a screwdriver. The dog point 6 has a smaller diameter than the threaded portion 5. A compression spring 8 is located between the bottom of the threaded bore 3 and the bottom of the screw 4. The threaded bore 3 has a length which, disregarding the length required for receiving the compressed spring 8, is greater than that of the screw 4. The passage orifice 9 in part 2 has a diameter which is smaller than that of the threaded portion 5 and larger than that of the dog point 6 of the screw 4.

Before assembly, the screw 4 is preferably sunk fully into the threaded bore 3. It should at least not protrude from the threaded bore 3 any more than a distance corresponding to the play between the mutually facing surfaces of the parts 1 and 2. The parts 1 and 2 are then pushed together until the passage orifice 9 lies over the screw 4. A screwdriver is then used to unscrew the screw 4 until its dog point 6 lies inside the passage orifice 9. If so desired, it can be turned until the shoulder of its threaded portion 5 bears sufficiently tightly on the edge of the passage orifice 9.

The latter is not absolutely essential since the spring 8 is present. This is because the latter pushes the screw 4 upward, so that it cannot sink back into the threaded bore 3 under the effect of any forces that occur.

Persons of ordinary skill in the art will be appreciate that the spring 8 which represented in the drawing as helical spring can be replaced by other types of springs or structures performing the same function as a spring in this type of structure, for example by a foam plug made of an elastic synthetic material.

What is claimed is:

1. A surgical implant or instrument comprising an upper part and a lower part each adapted for sliding on the other, the lower part having a blind threaded bore formed therethrough and the upper part having a passage orifice formed therein for receiving a fixing screw, a threaded fixing screw and an elastic device configured for pushing the fixing screw into a fixing position located between the bottom of the threaded bore and the bottom of the fixing screw,
  wherein the fixing screw is configured as a set screw and has a length such that the threaded bore can receive the fixing screw over its entire length beneath the upper part in the threaded bore,
  wherein the fixing screw comprises a dog point at an upper end of the fixing screw which is thinner than the threaded portion of the fixing screw and is configured for receiving a screwdriver, and
  wherein the diameter of the passage orifice has an inner diameter that is smaller than an inner diameter of the threaded bore and is larger than the diameter of the dog point.

2. The implant or instrument of claim 1, wherein the fixing screw and the threaded bore comprise interacting limit stops formed to secure the fixing screw against downward removal from the threaded bore.

3. The implant or instrument of claim 2, wherein the elastic device is a helical spring.

4. The implant or instrument of claim 2, wherein the elastic device is a foam plug made of an elastic synthetic material.

5. The implant or instrument of claim 2, wherein the elastic device is located between the bottom of the threaded bore and the bottom of the fixing screw.

6. The implant or instrument of claim 3, wherein the dog point comprises a groove, slit or hexagon socket configured for receiving a screwdriver.

7. The implant or instrument of claim 1, wherein the elastic device is a helical spring.

8. The implant or instrument of claim 1, wherein the elastic device is a foam plug made of an elastic synthetic material.

9. The implant or instrument of claim 1, wherein the dog point comprises a groove, slit or hexagon socket configured for receiving a screwdriver.

* * * * *

UNITED STATES PATENT AND TRADEMARK OFFICE
CERTIFICATE OF CORRECTION

PATENT NO. : 7,217,057 B2 Page 1 of 1
APPLICATION NO. : 11/058694
DATED : May 15, 2007
INVENTOR(S) : Arnold Keller It is certified that error appears in the above-identified patent and that said Letters Patent is hereby corrected as shown below:

In Claim 6, column 4, line 7, delete "3" and replace with --2--.

Signed and Sealed this

Thirteenth Day of November, 2007

JON W. DUDAS
*Director of the United States Patent and Trademark Office*